US008231790B2

(12) United States Patent
Yanagita

(10) Patent No.: US 8,231,790 B2
(45) Date of Patent: Jul. 31, 2012

(54) PROCESS FOR PRODUCING AN ANION ADSORBENT AND ANION ADSORBENT PRODUCED BY SAID PROCESS

(75) Inventor: Tomotaka Yanagita, Tokyo (JP)

(73) Assignee: Createrra Inc., Tokyo (JP)

( * ) Notice: Subject to any disclaimer, the term of this patent is extended or adjusted under 35 U.S.C. 154(b) by 656 days.

(21) Appl. No.: 12/308,336

(22) PCT Filed: Jun. 29, 2006

(86) PCT No.: PCT/JP2006/312964
§ 371 (c)(1),
(2), (4) Date: Dec. 12, 2008

(87) PCT Pub. No.: WO2008/001442
PCT Pub. Date: Jan. 3, 2008

(65) Prior Publication Data
US 2010/0230360 A1    Sep. 16, 2010

(51) Int. Cl.
*B01J 20/00*     (2006.01)
*C02F 1/42*      (2006.01)
(52) U.S. Cl. ................. 210/683; 210/688; 502/406
(58) Field of Classification Search ............ 502/406; 210/683, 688
See application file for complete search history.

(56) References Cited

U.S. PATENT DOCUMENTS

| 7,291,578 B2 * | 11/2007 | SenGupta et al. ............ 502/402 |
| 2002/0070172 A1 | 6/2002 | Schlegel |
| 2004/0186073 A1 | 9/2004 | Seidel et al. |
| 2008/0197081 A1 * | 8/2008 | Gadgil ......................... 210/688 |

FOREIGN PATENT DOCUMENTS

| GB | 748024 | 4/1956 |
| JP | 56-069229 | 6/1981 |
| JP | 61-153192 | 7/1986 |
| JP | 2-077266 | 3/1990 |
| JP | 3-182259 | 8/1991 |
| JP | 5-155776 | 6/1993 |
| JP | 6-122519 | 5/1994 |
| JP | 7-002903 | 1/1995 |
| JP | 8-024634 | 1/1996 |
| JP | 9-327694 | 12/1997 |
| JP | 2003-334542 | 11/2003 |
| JP | 2004-113885 | 4/2004 |
| JP | 2004-509752 | 4/2004 |
| JP | 2004-255376 | 9/2004 |
| JP | 2004-298668 | 10/2004 |
| JP | 2006-124239 | 5/2006 |

OTHER PUBLICATIONS

Henderson, et al., The impact of ferrous ion reduction of chlorite ion on drinking water process performance, Water Res. 35: 4464-4473 (2001).*

(Continued)

*Primary Examiner* — Chester Barry
(74) *Attorney, Agent, or Firm* — Jordan and Hamburg LLP

(57) ABSTRACT

A novel anion adsorbent with extremely high anion adsorptive power, composed mainly of iron as a metal excellent in biosafety, is provided. The anion adsorbent contains, as an active ingredient, amorphous ferric hydroxide produced under such conditions that a ferrous species is present.

26 Claims, 4 Drawing Sheets

OTHER PUBLICATIONS

Enver Murad, et al., "Jarosite, schwertmannite, goethite, ferrihydrite and lepidocrocite: the legacy of coal and sulfide ore mining", Supersoil, 2004, p. 3, 4th Paragraph.

Vicenzo Savica, et al.; "Phosphate binders and management of hyperphosphataemia in end-stage renal disease", Nephrology, Dialysis, Transplantation: Official Publication of the European Dialysis and Transplant Association, vol. 21, No. 8, Aug. 2006, pp. 2065-2068, XP002546960.

T. Yamaguchi, et al.; "Oral Phosphate Binders: Phosphate Binding Capacity of Iron (III) Hydroxide Complexes Containing Saccharides and Their Effect on the Urinary Excretion of Calcium and Phosphate in Rats"; Renal Failure Sep. 1999, vol. 21, No. 5, Sep. 1999, pp. 453-468, XP0009123066.

Satoshi Ida, et al.,; "Keiko Phosphorous Kyuchakuzai to shite no Hishoshitsu Suisankatetsu (III)", Journal of the Chemical Society of Japan, 1995, No. 1, pp. 19-24 Amorphous Iron (III) Hydroxide as Phosphor Adsorption Agent for Oral Administration.

Tatsuaki Yamaguchi, et al.; "Glucosamine Tenka ni yoru Muteikei Suisankatetsu no Gosei to Keiko Phosphorous Kyuchakuzai to shite no Hyoka", Dai 72, Kai CSJ: The Chemical Society of Japan Koen Yokoshu, 1997, p. 1271 (lecture No. 4K107) 4K107 Synthesis of Amorphous Iron Hydroxide by addition of Glucosamine and Its Evaluation as Phosphate Adsorption Agent for Oral Administration.

* cited by examiner

US 8,231,790 B2

PROCESS FOR PRODUCING AN ANION ADSORBENT AND ANION ADSORBENT PRODUCED BY SAID PROCESS

BACKGROUND OF THE INVENTION

The present invention relates to anion adsorbents capable of adsorbing various anions that are harmful to human and environment (negatively charged ions, examples of which include inorganic or organic anions, such as phosphate, arsenate or fluorine ions) with high efficiency. More specifically, the present invention relates to anion adsorbents useful as water or soil purifiers for removing such harmful anions from water or soil, for example.

In recent years, a phenomenon, so-called eutrophication, which is attributable to a rapid increase in burden of nitrogen and/or phosphorus, has been a concern in view of environmental conservation measures. As countermeasures to phosphoric acid as a factor of eutrophication, various phosphorus adsorbents such as those composed of granulated coal ash and those produced by mixing and firing volcanic ash and ferrous sulfate have been proposed, as described in Patent References 1 and 2.

Further, with respect to arsenate ion ($AsO_4^{3-}$) and arsenite ion ($AsO_2^-$) that are toxic anions present in water, the water quality standard was revised in 1993 to a more stringent value of no more than 10 μg As/l. As such, techniques for enabling highly efficient removal of arsenic in water are needed to be established. As a process for removing arsenate and arsenite ions in the prior art, such a procedure is known that metal salts, such as calcium, iron and aluminum salts are added to arsenic-containing water to produce hydroxides of such metals and then the arsenic oxide is coprecipitated with the metal hydroxides for removal (see the section "Prior Art" of Patent Reference 3).

Patent Reference 1: Japanese Unexamined Patent Publication No. 2004-113885

Patent Reference 2: Japanese Unexamined Patent Publication No. 2004-298668

Patent Reference 3: Japanese Unexamined Patent Publication No. 1997-327694

SUMMARY OF THE INVENTION

When conventional anion removers, for example, are used for water or soil purification, however, no single anion removers capable of effectively removing multiple toxic anions by small loading exist. For the purpose of removing these toxic anions to a degree in accordance to a recent increase in consciousness toward environment, therefore, multiple removers suitable for anions to be removed must be used in combination or a single anion remover must be used in large quantity. It is therefore the object of the present invention to provide anion adsorbents which, when used even in small quantity, are capable of effectively removing multiple toxic anions and are also useful as water or soil purifiers.

The present invention (1) is an anion adsorbent containing ferric hydroxide as produced under such conditions that a ferrous species is present.

The present invention (2) is the anion adsorbent according to the invention (1) wherein the ferric hydroxide is produced by adding to an aqueous solution of ferrous iron an oxidizing agent in an amount less than the equivalent amount of the ferrous iron and then adding an alkali in such a manner that its pH at the end of the reaction may be adjusted in the range of 1.5 to 5.5 (preferably in the range of 1.5 to 4.0 and more preferably in the range of 2.0 to 3.5).

The present invention (3) is the anion adsorbent according to the invention (1) wherein the ferric hydroxide is produced by adding an oxidizing agent to an aqueous solution of ferrous iron in such a manner that its redox potential may be brought in the range of +400 to 770 mV (preferably in the range of +500 to 730 mV and more preferably in the range of +600 to 700 mV) and then adding an alkali in such a manner that its pH at the end of the reaction may be adjusted in the range of 1.5 to 5.5 (preferably in the range of 1.5 to 4.0 and more preferably in the range of 2.0 to 3.5).

The present invention (4) is the anion adsorbent according to the invention (1) wherein the ferric hydroxide is produced by adding to an aqueous solution of ferrous iron an oxidizing agent in an amount less than the equivalent amount of the ferrous iron in such a manner that its redox potential may be brought in the range of +400 to 770 mV (preferably in the range of +500 to 730 mV and more preferably in the range of +600 to 700 mV) and then adding an alkali in such a manner that its pH at the end of the reaction may be adjusted in the range of 1.5 to 5.5 (preferably in the range of 1.5 to 4.0 and more preferably in the range of 2.0 to 3.5).

The present invention (5) is the anion adsorbent according to any one of the inventions (2) to (4) wherein the oxidizing agent is a hypochlorite.

The present invention (6) is the anion adsorbent according to any one of the inventions (1) to (5) wherein the ferric hydroxide is amorphous.

The present invention (7) is the anion adsorbent according to any one of the inventions (1) to (6) further including glycerin.

The present invention (8) is the anion adsorbent according to any one of the inventions (1) to (7) for adsorbing phosphate, arsenate or arsenite ions.

The present invention (9) is a water or soil purifier containing the anion adsorbent according to any one of the inventions (1) to (8).

The present invention (10) is a process for producing an anion adsorbent containing ferric hydroxide, which comprises the steps of adding to an aqueous solution of ferrous iron an oxidizing agent in an amount less than the equivalent amount of the ferrous iron and then adding an alkali in such a manner that its pH may be adjusted in the range of 1.5 to 5.5 (preferably in the range of 1.5 to 4.0 and more preferably in the range of 2.0 to 3.5).

The present invention (11) is a process for producing an anion adsorbent containing ferric hydroxide, which comprises the steps of adding an oxidizing agent to an aqueous solution of ferrous iron in such a manner that its redox potential may be brought in the range of +400 to 770 mV (preferably in the range of +500 to 730 mV and more preferably in the range of +600 to 700 mV) and then adding an alkali in such a manner that its pH may be adjusted in the range of 1.5 to 5.5 (preferably in the range of 1.5 to 4.0 and more preferably in the range of 2.0 to 3.5).

The present invention (12) is a process for producing an anion adsorbent containing ferric hydroxide, which comprises the steps of adding to an aqueous solution of ferrous iron an oxidizing agent in an amount less than the equivalent amount of the ferrous iron in such a manner that its redox potential may be brought in the range of +400 to 770 mV (preferably in the range of +500 to 730 mV and more preferably in the range of +600 to 700 mV) and then adding an alkali in such a manner that its pH may be adjusted in the range of 1.5 to 5.5 (preferably in the range of 1.5 to 4.0 and more preferably in the range of 2.0 to 3.5).

The present invention (13) is the process according to any one of the inventions (10) to (12) wherein the oxidizing agent is a hypochlorite.

The present invention (14) is the process according to any one of the inventions (10) to (13) wherein the ferric hydroxide is amorphous.

The present invention (15) is the process according to any one of the inventions (10) to (14) including the step of adding glycerin.

The present invention (16) is the process according to any one of the inventions (10) to (15) further including the step of dehydration, freeze-drying or spray-drying.

The present invention (17) is the process according to the invention (16) wherein, after the step for pH adjustment, the step of adding glycerin is performed before, during or after the step of dehydration, freeze-drying or spray-drying.

The present invention (18) is the process according to any one of the inventions (10) to (17) wherein the anion adsorbent is for adsorbing phosphate, arsenate or arsenite ions.

The present invention (19) is the process according to any one of the inventions (10) to (18) wherein the anion adsorbent is a water or soil purifier.

Terms as used herein will now be defined with respect to their meanings. A "ferrous species" refers to a substance in which iron is present as having a valence of two, such as a ferrous ion or ferrous compound (for example, ferric hydroxide). An "anion" for which "anion adsorbent" is intended refers to an inorganic or organic anion such as phosphate, arsenate, arsenite or fluorine ion and one or more of such anions in conjunction with other substances (not limited to anions) may also be encompassed in the concept. An "aqueous solution of ferrous iron" is not particularly limited as along as it is an aqueous solution in which ferrous ions are present and may contain other substances. An "oxidizing agent" is not particularly limited, examples of which may include hypochlorites, hydrogen peroxide and calcium hydroperoxide, hypochlorites being preferable.

DETAILED DESCRIPTION OF THE INENTION

Figure 1:
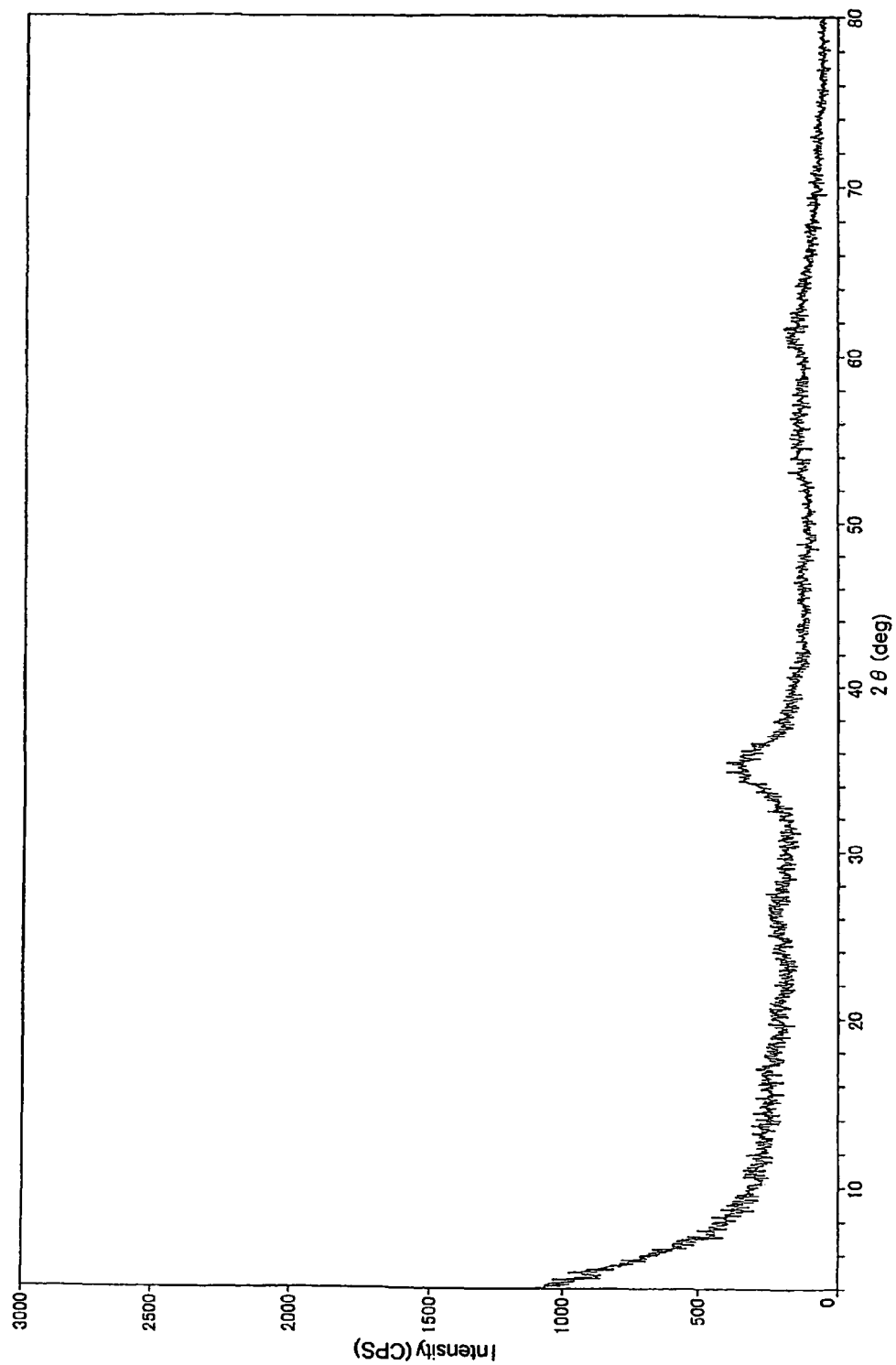
FIG. 1 is a chart illustrating X-ray diffractometry for Sample No. 1.

A best mode of the present invention will be described below. The technical purview of the present invention is in no way limited to such a best mode.

The present anion adsorbent includes amorphous ferric hydroxide as produced under such conditions that a ferrous species (for example, ferrous hydroxide) is present. Although the active ingredient exhibiting a high anion adsorptive power is amorphous ferric hydroxide, not any of amorphous ferric hydroxide can achieve such an effect. For example, ferric hydroxide produced by adding caustic soda to a solution of ferric iron or commercially available ferric hydroxide will not exhibit such a high anion adsorptive power (see Examples). On the basis of Eh (redox potential) vs pH charts for $Fe^{2+}$-$Fe(OH)_3$ systems, the present ferric hydroxide is produced under extremely unstable conditions where iron ions are present as ferric ions while remaining under Eh vs pH conditions where they remain as ferrous iron when they are present as a stable chemical species. The present ferric hydroxide therefore includes ferrous iron in the produced precipitate and is in an unstable and extremely amorphous state. The present ferric hydroxide is therefore characterized in that the bond —Fe—O—Fe—O—Fe is unstable and easily cut off and it is presumed that newly produced Fe—OH groups react with anions while bonds are cut off, exhibiting remarkably high adsorptive power.

The chemical structure of ferric hydroxide is unclear. On the basis of experimentation results and the like, however, it has presumably the structure as described below (the ferric hydroxide according to the present invention is not, however, limited to such a presumed formation). Specifically, the present ferric hydroxide essentially contains ferric iron and has oxygen atoms or hydroxyl groups that are hexacoordinated to iron atoms so that the hexacoordinated irons are presumably linked via oxygen atoms. It is then presumed that certain water molecules present around such iron atoms will have influence on the bond between the iron atoms and the oxygen atoms, consequently destabilizing the bond. It is then believed that, as a result of replacement of the hydroxyl groups or the destabilized oxygen atoms coordinated to the iron atoms with anions (for example, phosphate ions) the iron atoms will bond with those anions (phosphate ions). Under such assumption, a preferable formation is one in which —Fe—O—Fe—O—Fe—(cluster) has a moderate size due to the presence of moderate hydroxyl groups.

In a process for producing the present anion adsorbent, ferrous iron is reacted with an oxidizing agent (for example, sodium hypochlorite) to obtain ferric hydroxide as described, below. The reaction scheme for such a redox reaction is shown below, wherein ferric hydroxide is abbreviated as "Fe(OH)$_3$" for ease of understanding.

$2Fe^{++} + NaClO + 5H_2O \rightarrow 2Fe(OH)_3 + NaCl + 4H^+$   Chemical Formula 1

As shown above, one mole of hypochlorite reacts with two moles of ferrous iron (in other words, one mole of hypochlorite is equivalent in amount to two moles of ferrous iron). In the process for production, such conditions are then established that the ferrous iron may not completely be oxidized into the ferric iron by reducing the amount of the oxidizing agent to less than the equivalent amount of the ferrous iron (for example, to less than one mole of hypochlorite, in the case of two moles of ferrous iron) as described below.

Terms such as "amorphous" or "extremely high in amorphousness" mean that X-ray powder diffractometry using Kα ray of Cu as an X-ray source shows at least one non-crystalline halo pattern in the range of 5° to 80° by 2θ value, with no apparent crystalline peaks. Slight crystalline peaks may be observed in non-crystalline halo patterns depending on starting materials or the like during production. In such cases, the crystalline peak intensities observed in the range of 5° to 80° by 2θ value in X-ray powder diffractometry using Kα ray of Cu as an X-ray source may be allowed if they are at or below 5% in relation to crystalline peaks for corresponding crystalline reference material (% X-ray diffraction intensity/reference material). Specific % X-ray diffraction intensity/reference materials which may be used include those given by the formula below in accordance with ASTM (American Society for Testing and Materials) D3906. The number of crystalline peaks used for calculation of integrated reflection intensities is not particularly limited, but is preferably in the range of 1 to 8.

$$(\text{\% X-ray diffraction intensity/reference material}) = \{(S_X)/(S_R)\} \times 100 \quad \text{Equation 2}$$

wherein $S_X$ represents an integrated reflection intensity of a sample, and $S_R$ represents an integrated reflection intensity of a reference material.

Thus, although the active ingredient is ferric hydroxide, ferrous species are inevitably contained since the production is performed under such conditions that ferrous species (for example, ferrous hydroxide) are present. The content of such ferrous species is not particularly limited and usually 5% by weight or less, preferably from 0.01 to 4% by weight and more preferably from 0.1 to 2% by weight on the basis of dry weight (furnace-dried at 105° C. for 2 h). The ferrous species are inevitably contained during production and such ingredients may, however, be removed by washing.

Further, the present anion adsorbent may contain crystalline ferric hydroxide as long as amorphous ferric hydroxide as the active ingredient is present. In such cases, the amorphous ingredient comprises preferably 30% or more, more preferably 50% or more and even more preferably 75% or more.

It is preferable that the present anion adsorbent further contains glycerin. Depending on the method of drying or aging, the ferric hydroxide causes its OH groups attached to irons of —Fe—O—Fe—O—Fe— to be dehydrated and assumes a stable condition through growth of clusters or otherwise, possibly decreasing its adsorptive power. Therefore, admixing glycerin to wetted ferric iron makes it difficult for dehydration of OH groups to occur when it gets dry so that a decrease in adsorptive power may remarkably be inhibited. The content of glycerin is preferably 20% by weight or less on the basis of dry weight (furnace-dried at 105° C. for 2 h).

A process for producing the anion adsorbent according to the best mode will then be described. The present anion adsorbent is obtained by (Step 1A) adding to an aqueous solution of ferrous iron an oxidizing agent (for example, an aqueous hypochlorite solution) in an amount less than the equivalent amount of the ferrous iron (preferably from 0.3 to 0.95 and more preferably from 0.4 to 0.8) or (Step 1B) adding an oxidizing agent (for example, an aqueous hypochlorite solution) to an aqueous solution of ferrous iron in such a manner that its redox potential may be brought in the range of +400 to 770 mV (preferably in the range of +500 to 730 mV and more preferably in the range of +600 to 700 mV) and then (Step 2) adding an alkali (preferably a caustic alkali) in such a manner that its pH may be adjusted in the range of 1.5 to 5.5 (preferably in the range of 1.5 to 4.0 and more preferably in the range of 2.0 to 3.5). The order of Step 1A or Step 1B and Step 2 is important. If reversed, anion adsorbents having high adsorptive power could not be obtained. Each condition will be described below.

First, ferrous salts which may be used in the aqueous solution of ferrous iron are not particularly limited as long as they are water-soluble, examples of which may include ferrous sulfate, ferrous chloride and ferrous nitrate. Ferrous sulfate is preferable because filtration of precipitate is easy. Further, the concentration of ferrous ions in the aqueous solution of ferrous iron is preferably from 0.05 to 2 M.

Next, oxidizing agents which may be used are not particularly limited and are preferably hypochlorites. Examples of hypochlorites may include sodium hypochlorite and calcium hypochlorite, sodium hypochlorite being particularly preferable. The concentration of a hypochlorite in an aqueous hypochlorite solution is not particularly limited and commercially available solutions with concentrations of 5 to 10% are usable.

When Step 1A is adopted, the amount of an oxidizing agent is to be less than the equivalent amount of ferrous iron in an aqueous solution of ferrous iron. The amount of the oxidizing agent is preferably from 0.3 to 0.95 and more preferably from 0.4 to 0.8 in equivalence ratio in relation to the amount of the ferrous iron.

Also, when Step 1B is adopted, an oxidizing agent (for example, an aqueous hypochlorite solution) is added to an aqueous solution of ferrous iron in such a manner that its redox potential may be brought in the range of +400 to 770 mV (preferably in the range of +500 to 730 mV and more preferably in the range of +600 to 700 mV). It is preferable that the addition of a solution of oxidizing agent (for example, an aqueous hypochlorite solution) is made dropwise while stirring.

Steps 1A and 1B may not necessarily be independent steps, so that embodiments in which performing Step 1A results in performing Step 1B and vice versa may be included.

Next, after adding a predetermined amount of oxidizing agent in Step 1A or after confirming that the redox potential has settled within the specified range, Step 2 of adding an alkali will be performed. Alkalis are not particularly limited and preferably are caustic alkalis. Examples of caustic alkalis may include caustic soda and caustic potassium, caustic soda being preferable. In addition, the concentration of alkali (preferably, the concentration of caustic alkali) is from 0.5 to 5 N for example. Then, to the solution to which the predetermined amount of oxidizing agent has been added (Step 1A) or the solution whose redox potential has settled within the specified range (Step 1B) an aqueous alkali solution (preferably, an aqueous caustic alkali solution) is added in such a manner that its pH may be brought in the range of 1.5 to 5.5 (preferably in the range of 1.5 to 4.0 and more preferably in the range of 2.0 to 3.5). Through this procedure, amorphous ferric hydroxide will precipitate, providing the present anion adsorbent.

The present anion adsorbent is preferably in dry form for the ease of handling. A method for drying is preferably dehydration, freeze-drying or spray-drying, through which dehydration from the Fe—OH bond is reduced during drying so that anion adsorptive power may remain high.

Further, admixing glycerin before, during or after drying can minimize a decrease in anion adsorptive power. The amount of glycerin added is 20% or less (preferably from 3 to 7%) on the basis of dry weight (furnace-dried at 105° C. for 2 h). The time for admixing glycerin is not particularly limited and is preferably after pH adjustment and before drying.

Next, description will be made on uses and methods for use of the present anion adsorbent. The present anion adsorbent is not particularly limited in the field of application as long as removal of anions is desired and is useful, for example, as a water purifier or soil purifier. Such uses will be described in detail below.

First, water purifiers are applicable in places where water purification is desired such as rivers, oceans, lakes and aquariums and ponds for fish culture. The amount used of the water purifier according to the present invention varies according to the specific water to be purified, the concentration of anions (for example, phosphate, arsenate and arsenite ions) in water and the like and is appropriately from 100 to 1,000 g in relation to 1 $m^3$ of water, in general. Further, the water purifier according to the present invention may be used in a variety of ways depending on the situation, including sprinkling it directly or forcibly circulating water to be purified through a cylinder loaded with it.

Next, soil purifiers are applicable for soils where contamination is of concern (including sludge and dredged matter). The amount used of the soil purifier according to the present invention varies according to the specific soils to be purified, the concentration of anions (for example, phosphate, arsenate and arsenite ions) in soil and the like and is appropriately from 100 to 10,000 g in relation to 1 $m^3$ of soil when the soil contains 0.1 to 10 mg of contaminant per liter of soil. Also, examples of methods for mixing the soil purifier according to the invention with soil may include mixing soil and the soil purifier using various mixers or the like, pumping, jet injection, simply sprinkling it across the soil surface and using a sprinkler.

EXAMPLES

Production of Anion Adsorbent

6% sodium hypochlorite (active chlorine 5%) was added dropwise while stirring to 800 ml of a 0.1 M aqueous ferrous sulfate solution (amount added dropwise=29.8 g, equivalent ratio=0.588) in such a manner that its redox potential was 650 mV and the solution was left for three minutes while stirring. 1N caustic soda was added to the solution until its pH was stabilized at 2.7 to obtain the anion adsorbent according to the example. The pH at the end of the reaction was 2.7 and the redox potential was +584 mV.

Component Analysis (1) Quantitative Analysis according to Fe Formation

For the anion adsorbent obtained above, quantitative analysis was performed with respect to T-Fe, M-Fe, $Fe^{2+}$ and $Fe^{3+}$ ("T" means total and "M" means metal). For T-Fe, stannous chloride reduction-potassium dichromate titration was used for measurement, for M-Fe, mercuric chloride dissolution-potassium dichromate titration was used for measurement, for $Fe^{2+}$, inert gas-filled acid dissolution-potassium dichromate titration was used for measurement and, for $Fe^{3+}$, calculations were made according to the equation $[Fe^{3+}=T-Fe-(M-Fe+Fe^{2+})]$. The results are summarized in Table 1. Sample No. 1 is a paste-like anion adsorbent and Sample No. 2 is a freeze-dried anion adsorbent.

TABLE 1

Quantitative Analysis Result (unit: wt %)

| sample | T-Fe | M-Fe | $Fe^{2+}$ | $Fe^{3+}$ |
|---|---|---|---|---|
| No. 1 | 43.6 | less than 0.1 | 0.5 | 43.1 |
| No. 2 | 43.8 | less than 0.1 | 1.0 | 42.7 |

(2) Identification of Compositional Phase by X-ray Diffractometry (XRD)

Equipment: Type RINT-2200, Rigaku Corporation

Tube: Cu

Voltage-Current: 40 kV-40 mA

Scan Rate: 4°/min

Scan Range: 5° to 80° (2θ)

Figure 2:
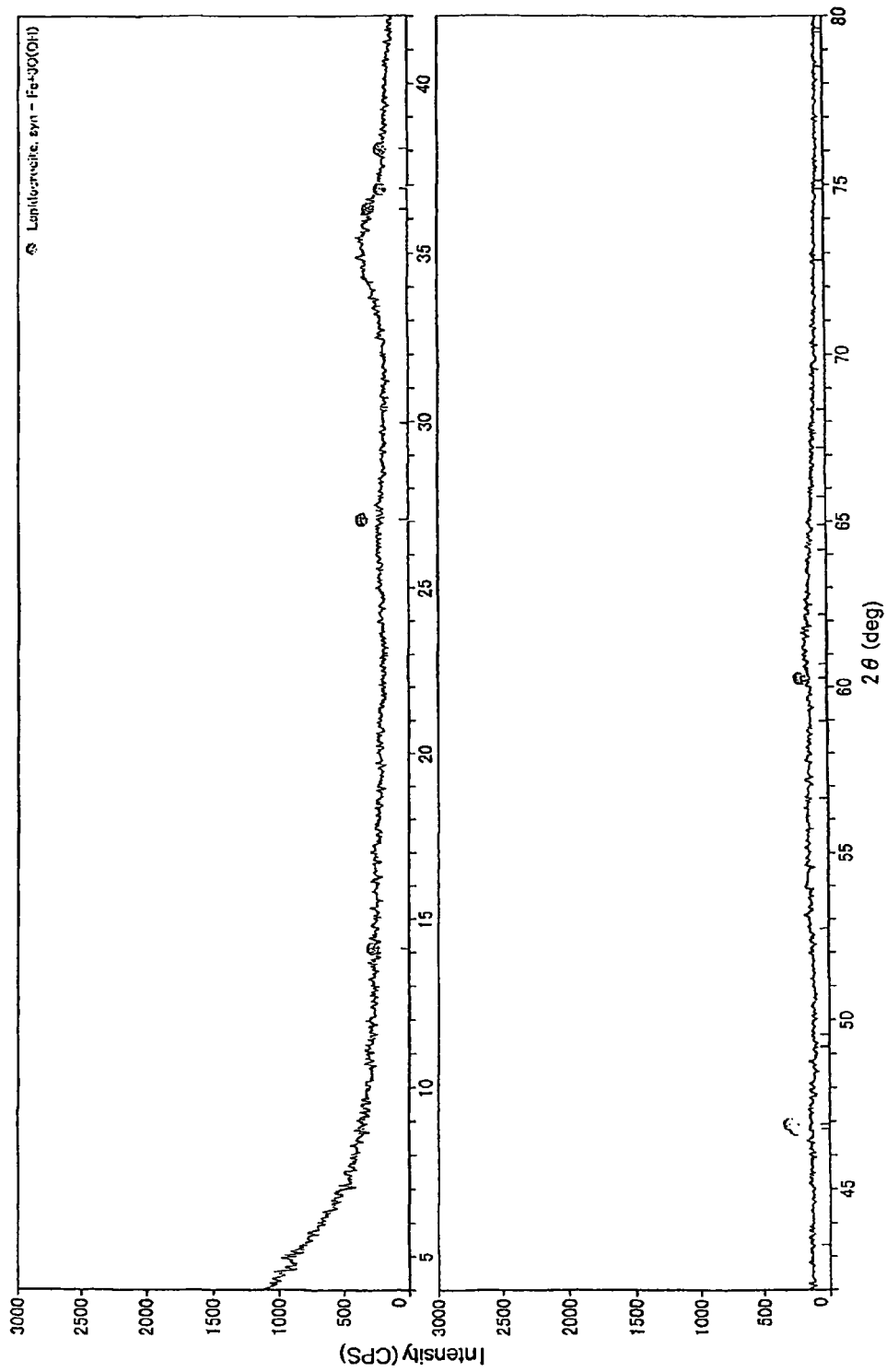
FIG. 2 is a chart illustrating X-ray diffractometry for Sample No. 1.
Figure 3:
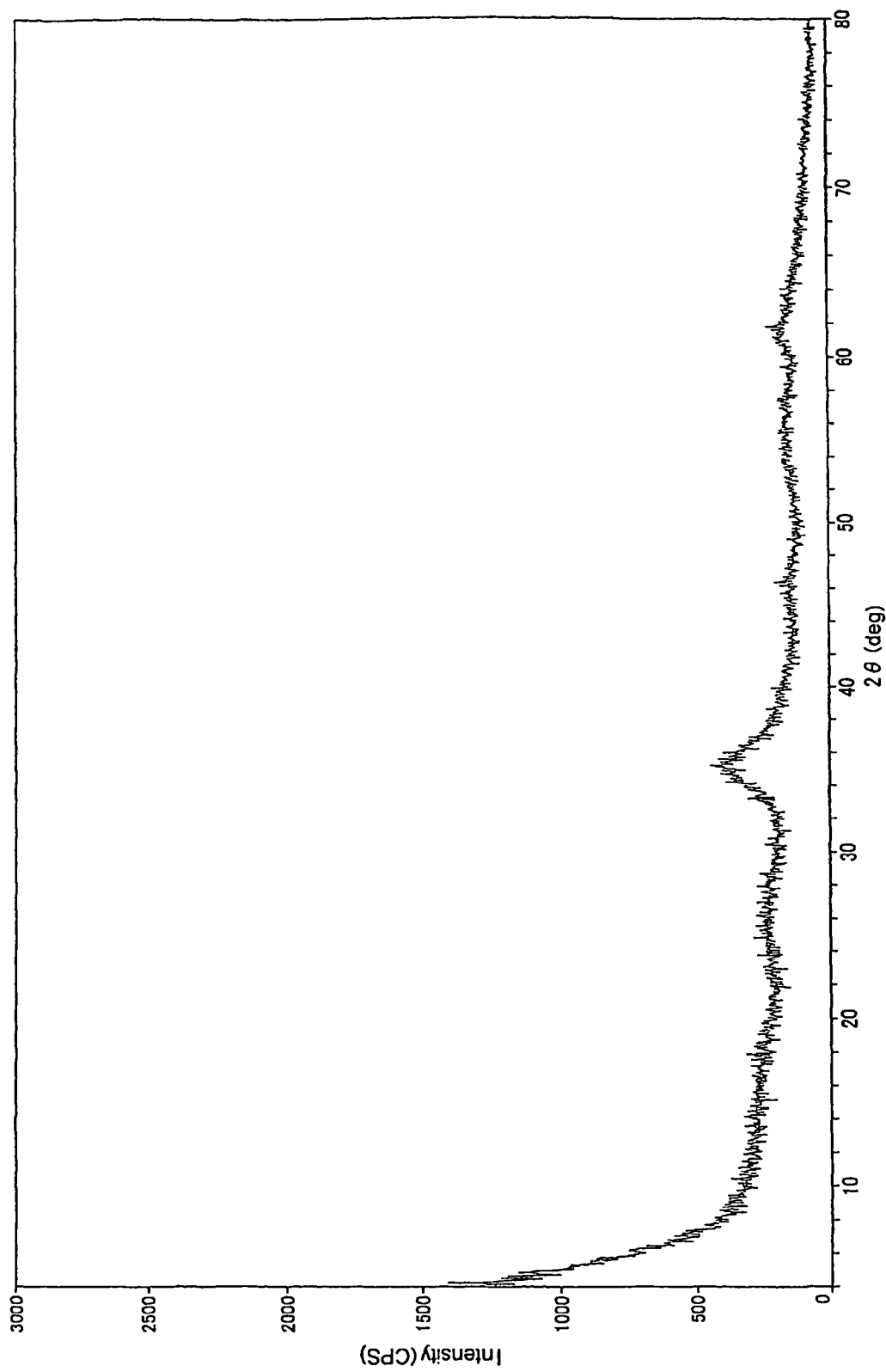
FIG. 3 is a chart illustrating X-ray diffractometry for Sample No. 2.
Figure 4:
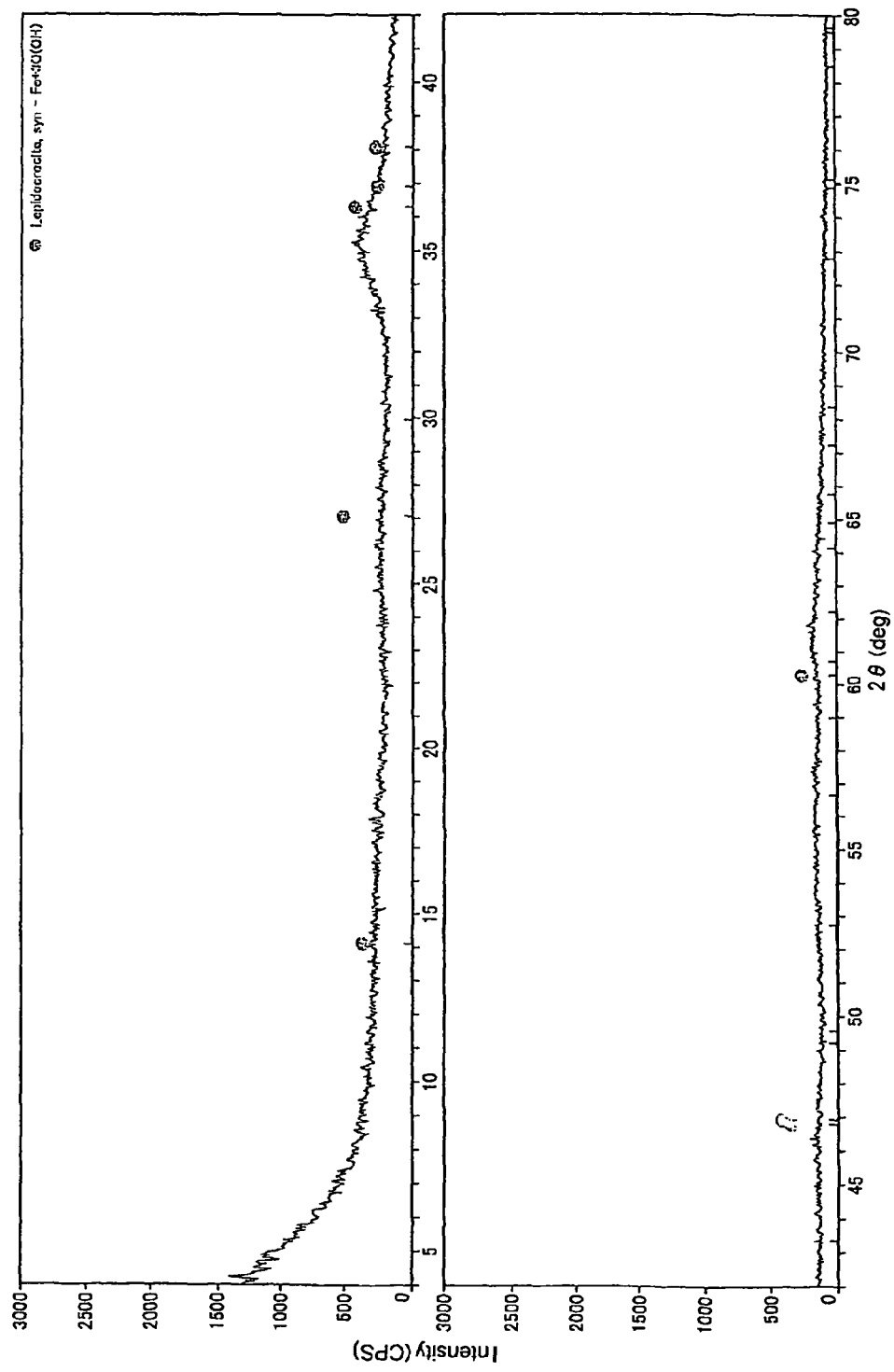
FIG. 4 is a chart illustrating X-ray diffractometry for Sample No. 2.

X-ray diffractometry experiment was performed under the measurement conditions above. X-ray diffraction charts are shown in FIGS. 1 to 4 and the results of analysis are summarized in Table 2.

TABLE 2

X-ray Diffractometry Result

| compositional phase/sample name | relative intensity | |
|---|---|---|
|  | No. 1 | No. 2 |
| Lepidocrocite γ-FeOOH | (+) | (+) |
| amorphous ingredient | +++ | +++ | relative intensity:

++++ very high,

+++ high,

++ moderate,

+ low, (+) very low,

− undetectable

Based on the analysis results, lepidocrocite (γ-FeOOH) was detected as very low in intensity for both Samples No. 1 and No. 2. Also, both Samples showed generally broadened profiles except the diffraction peaks obtained in the X-ray diffraction charts, eliciting extremely high amorphousness.

Phosphorus Adsorption Test

For determining phosphorus adsorptive power, 20 ml of an ammonium phosphate solution (5.9 g P/l) were added to 0.5 g (dry weight) of the anion adsorbent according to the example and the solution was left for 24 hours with occasional shaking. The solution was then filtrated and the concentration of phosphorus in the filtrate was determined and calculated. For comparison, adsorptive power was also tested in a similar procedure for ferric hydroxide produced by rapidly stirring 1N NaOH into a 1M aqueous $FeCl_3$ solution in such a manner that its pH may be brought in the range of 7.5 to 8.0 and hydrous iron oxide (commercial product) produced through dehydration of ferric hydroxide. The results are summarized in Table 3

TABLE 3

|  | example | ferric hydroxide | commercial product (hydrous iron oxide) |
|---|---|---|---|
| phosphorus adsorptive power | 156 g/kg | 56 g/kg | 14.8 g/kg |

Example of Addition of Glycerin, etc.

Glycerin, ethanol and skimmed milk were added to the 70% hydrous anion adsorbent produced according to the above procedure each at 5% by weight of the anion adsorbent and were freeze-dried. Phosphorus adsorptive power of these dry products is summarized in Table 4.

TABLE 4

| products | hydrous | freeze-dried | 5% glycerin added, freeze-dried | 5% EtOH added, freeze-dried | 5% skimmed mild added, freeze-dried |
|---|---|---|---|---|---|
| phosphorus adsorptive power | 156 g/kg | 102 g/kg | 130 g/kg | 117 g/kg | 123 g/kg |

Arsenious Acid and Arsenic Acid Adsorption Test

An aqueous $NaAsO_2$ solution with $As^{3+}$ concentration of 60 ppm was used as arsenious acid. 0.20 g of the anion adsorbent according to the example was added to 20 ml of this aqueous solution and the solution was shaken for 20 hours. Arsenious acid in the solution after shaking was not more than the measurement limit. Adsorption of arsenious acid by the anion adsorbent according to the example was therefore not less than 11.9 mg/g. Also, an aqueous $Na_2HAsO_2 \cdot 7H_2O$ solution with $As^{5+}$ concentration of 80 ppm was used as arsenic acid. 0.20 g of the anion adsorbent according to the present invention was added to 20 ml of this aqueous solution and the solution was shaken for 20 hours. Arsenic acid in the solution after shaking was not more than the measurement limit. Adsorption of arsenic acid by the anion adsorbent according to the present invention was therefore not less than 15.9 mg/g.

Test for Confirming Soil Improvement Effect

A suspension was produced from a mixture of a ferrous sulfate solution and sodium hypochlorite using caustic soda to adjust its pH at 2.7 and 5 g of the suspension in terms of dry weight of ferric hydroxide were sprinkled to 1 kg of dredged matter having arsenic elution of 1.47 mg/l and were thoroughly mixed. Arsenic elution from the mixture of the dredged matter and the ferric hydroxide-containing suspension was not more than the detection limit.

The invention claimed is:

1. A process for producing an anion adsorbent comprising ferric hydroxide, which comprises the steps of adding to an aqueous solution of ferrous iron an oxidizing agent in an amount less than the equivalent amount of the ferrous iron and/or which brings redox potential of the solution to a value in a range of +400 to 770 mV and then adding to the solution an alkali to adjust pH of the solution to a value in a range of 1.5 to 5.5.

2. An anion adsorbent comprising ferric hydroxide containing a ferrous species, which is produced by the process of claim 1.

3. A method of adsorbing anions from a medium containing the anions, comprising contacting the medium with an anion adsorbent according to claim 2.

4. The method according to claim 3, wherein the ferrous species comprises a ferrous anion or ferrous compound.

5. The method according to claim 4, wherein the medium comprises soil or water.

6. The method according to claim 4 or 5, wherein the anions to be adsorbed are inorganic or organic.

7. The method according to claim 6, wherein the anions to be adsorbed are toxic to humans.

8. The method according to claim 6, wherein the anions to be adsorbed are at least one selected from the group consisting of phosphate, arsenate and arsenite ions.

9. A process according to claim 1, wherein the oxidizing agent is added to the solution in an amount which adjusts redox potential of the solution to a value in a range of +400 to 770 mV.

10. An anion adsorbent comprising ferric hydroxide containing a ferrous species, which is produced by the process of claim 9.

11. An anion adsorbent comprising amorphous ferric hydroxide containing a ferrous species, which is produced by the process of claim 9, wherein the oxidizing agent is a hypochlorite.

12. An anion adsorbent comprising ferric hydroxide containing a ferrous species and glycerin, which is produced by the process of claim 9, wherein the oxidizing agent is a hypochlorite.

13. A process according to claim 1, wherein the amount of the oxidizing agent added to the solution is less than the equivalent amount of the ferrous iron.

14. An anion adsorbent comprising ferric hydroxide containing a ferrous species, which is produced by the process of claim 13.

15. An anion adsorbent comprising amorphous ferric hydroxide containing a ferrous species, which is produced by the process of claim 13, wherein the oxidizing agent is a hypochlorite.

16. An anion adsorbent comprising ferric hydroxide containing a ferrous species and glycerin, which is produced by the process of claim 13, wherein the oxidizing agent is a hypochlorite.

17. The anion adsorbent according to any one of claims 2 to 14, wherein the ferric hydroxide is amorphous.

18. The anion adsorbent according to any one of claims 2 to 14, further comprising glycerin.

19. The process according to any one of claims 1 to 13, wherein the ferric hydroxide is amorphous.

20. The process according to any one of claims 1 to 13, further comprising the step of adding glycerin.

21. The process according to any one of claims 1 to 13, further comprising the step of dehydration, freeze-drying or spray-drying.

22. The process according to claim 21, wherein, after the step for pH adjustment, the step of adding glycerin is performed before, during or after the step of dehydration, freeze-drying or spray-drying.

23. The process according to any one of claims 1 to 13, wherein the oxidizing agent is a hypochlorite.

24. An anion adsorbent comprising ferric hydroxide containing a ferrous species, which is produced by the process of claim 23.

25. An anion adsorbent comprising amorphous ferric hydroxide containing a ferrous species, which is produced by the process of claim 1, wherein the oxidizing agent is a hypochlorite.

26. An anion adsorbent comprising ferric hydroxide containing a ferrous species and glycerin, which is produced by the process of claim 1, wherein the oxidizing agent is a hypochlorite.

* * * * *